United States Patent [19]
Zhang et al.

[11] Patent Number: 6,150,098
[45] Date of Patent: Nov. 21, 2000

[54] METHODS FOR IDENTIFYING NOVEL SECRETED MAMMALIAN POLYPEPTIDES

[75] Inventors: Ke Zhang; Robert Pacifici, both of Thousand Oaks, Calif.

[73] Assignee: Amgen Inc., Thousand Oaks, Calif.

[21] Appl. No.: 09/026,958

[22] Filed: Feb. 20, 1998

[51] Int. Cl.$^7$ .............. C12Q 1/68; C12N 15/63; C07H 21/04
[52] U.S. Cl. .......... 435/6; 435/320.1; 536/23.4; 536/23.1
[58] Field of Search ............ 435/6, 320.1; 536/23.1, 536/23.4

[56] References Cited

U.S. PATENT DOCUMENTS

| | | | |
|---|---|---|---|
| 4,419,446 | 12/1983 | Howley et al. | 435/68 |
| 4,923,808 | 5/1990 | Matteucci | 435/69.8 |
| 5,037,760 | 8/1991 | Smith et al. | 435/320.1 |
| 5,525,486 | 6/1996 | Honjo et al. | 435/69.1 |
| 5,536,637 | 7/1996 | Jacobs | 435/6 |
| 5,952,171 | 9/1999 | McCarthy et al. | 435/6 |

FOREIGN PATENT DOCUMENTS

| | | |
|---|---|---|
| 96/40904 | 12/1996 | WIPO . |
| 97/23614 | 7/1997 | WIPO . |
| WO9822491 | 5/1998 | WIPO . |

OTHER PUBLICATIONS

Chen et al. Nucleic Acids Research. 27 (4): 1219–1222, 1999.
Ausubel et al., eds Current Protocols in Molecular Biology, Current Protocols Press, (1994).
Berger and Kimmel, Methods in Enzymology: Guide to Molecular Cloning Techniques, vol. 152, Academic Press, Inc., San Diego, CA, (1987).
Delli–Bovi et al. Cell 50, 729–737 (1987).
Delli–Bovi et al. Mol. Cell. Biol. 8, 2933–2941 (1988).
Engels et al. Angew. Chem. Intl. Ed. 28:716–734 (1989).
Gething and Sambrook Nature, 293:620–625 (1981).
Imai et al. J. Biol. Chem. 271, 21514–21521 (1996).
Kaufman et al. Mol. Cell. Biol., 5:1750–1759 (1985).
Klein et al. Proc. Natl. Acad. Sci. USA 93, 7108–7113 (1996).
Millan, J. Biol. Chem. 261, 3112–3115 (1986).
Sambrook et al., Molecular Cloning: A Laboratory Manual, Cold Spring Harbor Laboratory Press, Cold Spring Harbor, NY, (1989).
Shirozu et al. Genomics 37, 273–280 (1996).
Talarico et al. Mol. Cell. Biol. 11, 1138–1145 (1991).
Urlaub and Chasin, Proc. Natl. Acad. Sci., USA, 77:4216–4220 (1980).
Wells et al. Gene 34:315 (1985).

*Primary Examiner*—Jeffrey Fredman
*Assistant Examiner*—Juliet C. Einsmann
*Attorney, Agent, or Firm*—Robert B. Winter; Steven M. Odre; Ron K. Levy

[57] ABSTRACT

Methods for identifying novel secreted mammalian proteins in mammalian host cells are described. Reporter polypeptides which allow detection of signal sequences by growth selection or by enzymatic activity are also described.

5 Claims, No Drawings

METHODS FOR IDENTIFYING NOVEL SECRETED MAMMALIAN POLYPEPTIDES

FIELD OF THE INVENTION

The invention relates to methods for identifying novel secreted mammalian proteins.

BACKGROUND OF THE INVENTION

Proteins destined for transport into or across cell membranes are usually translated with a signal sequence that directs the newly synthesized protein to the appropriate membrane translocation system. The primary structure of signal sequences is highly variable among different proteins. Signal sequences that target proteins for export from the cytosol generally contain a short stretch (7–20 residues) of hydrophobic amino acids. In most cases, the signal sequence is located at the amino terminus of a nascent protein and is proteolytically removed on the trans side of the membrane (e.g. lumen of endoplasmic reticulum, bacterial periplasm, intercisternal space of mitochondria and chloroplasts), although examples of mature proteins containing uncleaved or internal signal sequences have been described. Export signal sequences may be interchanged among different proteins, even proteins of different species of organisms.

Many secreted eucaryotic proteins interact with target cells to bring about physiological responses such as growth, differentiation and/or activation. These activities make secreted proteins biologically interesting molecules which are potentially valuable as therapeutics or as targets for ligands. Of the estimated 60,000 to 100,000 human genes, about 25% carry a signal peptide and only about 4% are secreted extracellularly. Clearly, approaches which allow rapid and accurate identification of secreted proteins are important tools for gene-based drug discovery programs.

With advances in techniques for sequencing cDNAs, many expressed sequence tags (ESTs) have been generated which have enhanced the process of identifying novel secreted proteins as compared to the conventional reverse genetics approaches. However, EST's are small random cDNA sequences and thus it becomes hard to identify secretion signal sequence that is normally present in the 5' end of cDNA encoding secreted protein. Moreover, after an EST carrying a potential secretion signal sequence is identified based on the homology search, it has to be authenticated in a functional assay. Thus a screen based on selection of functional secretion signals from random cDNA libraries would greatly simplify the process of obtaining novel secreted genes.

Secretion signal trap is one such method to clone 5' ends of cDNAs encoding for secreted proteins from a random cDNA library. Generally, signal trapping relies on secretion of a reporter polypeptide by signal sequences present in a cDNA library. The secreted reporter polypeptide may be detected by a variety of assays based upon growth selection, enzymatic activity or immune reactivity. Examples of signal trap cloning procedures include the following.

U.S. Pat. No. 5,536,637 and Klein et al. Proc. Natl. Acad. Sci. USA 93, 7108–7113 (1996) describe signal trap cloning in yeast using the yeast invertase polypeptide as a reporter.

Imai et al. J. Biol. Chem. 271, 21514–21521 (1996) describe signal trap cloning in mammalian cells using CD4 as a reporter and identifying signal sequences by screening for surface expression of CD4 antigen.

U.S. Pat No. 5,525,486, Shirozu et al. Genomics 37, 273–280 (1996) and Tashiro et al. Science 261, 600–603 (1993) describe signal trap cloning in mammalian cells and identify signal sequences by screening for surface expression of IL-2 receptor fusion proteins.

U.S. Pat. No. 5,037,760 describes signal trap cloning in Bacillus using α-amylase and β-lactamase as reporter genes.

Published PCT Application No. WO96/40904 describes signal trap cloning by selection for growth of factor-dependent cell lines and screening with tagging reagents for surface expression of growth factor receptors.

Previous approaches to identifying mammalian secreted and transmembrane protein by signal trapping in yeast and prokaryotic systems have a disadvantage in that the machinery that translocates proteins across the membrane of the endoplasmic reticulum (ER) and the mechanisms that process proteins in the ER-golgi are different in mammalian cells. For example, *Saccromyces cerivisiae* utilizes both a cotranslational and posttranslational mechanism to transport proteins containing signal sequences and mutants in the yeast SRP54 protein, which is integral to the cotranslational mechanism, are viable. Mammalian cells appear to have evolved a special dependence on the cotranslational mechanism and posttranslational modifications are more complex. Thus, many mammalian secreted or transmembrane proteins constructs may not express or sort properly in yeast and, conversely, many mammalian protein sequences appear to function aberrantly as signal sequences.

The above approaches to signal trapping in mammalian cells also lack a convenient selection method for signal sequences in mammalian host cells. Methods described to date involve screening many clones either by enzyme activity or immunoassay for secretion with no efficient way to select against clones not containing functional signal sequences. It would be desirable to provide positive selection for secretion from mammalian cells and reduce the need to screen all clones for signal sequences.

Accordingly, it is an object of the invention to provide signal trap vectors and related methods and compositions for rapidly and accurately identifying novel secreted proteins in mammalian host cells.

SUMMARY OF THE INVENTION

The invention provides a method for trapping signal sequence DNA from cDNA libraries comprising the steps of constructing a cDNA library in a signal trap vector for transfection into a mammalian host cell and detecting secretion of a reporter polypeptide. The signal trap vector contains DNA encoding a reporter polypeptide which lacks a functional signal sequence. Secretion of the reporter polypeptide is indicative of the presence of functional signal sequence and may be detected by a variety of methods, including growth under certain nutrient conditions, enzyme activity, or immune reactivity. A cDNA molecule encoding the full-length polypeptide containing the functional signal sequence is identified, cloned and expressed and the resulting polypeptide is isolated and purified.

Significantly, the present invention provides in part a method of selecting for signal sequences in mammalian cells by using a reporter polypeptide which stimulates growth of the host cell.

The invention provides for a method for identifying a secreted mammalian protein comprising the steps of:

a) constructing a mammalian cDNA library;

b) inserting the cDNA library of step (a) into a signal trap vector to generate a signal trap library, wherein the vector comprises DNA encoding a reporter polypeptide, wherein the reporter polypeptide is a secreted mammalian growth factor lacking a functional signal sequence;

c) amplifying the signal trap library of step (b);

d) transfecting the library of step (c) into a mammalian host cell lacking the functional reporter polypeptide of step (b);

e) selecting transfected mammalian cells from step (d) for growth in selective medium requiring secretion of the reporter polypeptide;

f) analyzing the DNA recovered from the transfected cells of step (e) which exhibit growth on the selective medium to determine whether a functional mammalian signal sequence is present; and g) screening a mammalian cDNA library to identify a full-length cDNA comprising the functional mammalian signal sequence of step (f).

The reporter polypeptides of the invention which detect signal sequences by growth selection include mammalian growth factors which stimulate cell proliferation by an autocrine mechanism. In one embodiment, the growth factors are secreted members of the fibroblast growth factor (FGF) family.

The invention also relates to a CDNA molecule encoding a novel secreted mammalian protein and a novel secreted mammalian protein identified by employing steps (a) through (g) as set forth above.

The invention provides for a method of identifying a novel secreted mammalian polypeptide comprising the steps of:

a) constructing a mammalian CDNA library;

b) isolating from the cDNA library of step (a) DNA fragments of a selected size;

c) inserting the DNA fragments of step (b) into a signal trap vector to generate a signal trap library, wherein the vector comprises DNA encoding a secreted human alkaline phosphatase lacking a functional signal sequence;

d) amplifying DNA from the signal trap library of step (c);

e) transfecting the amplified DNA of step (d) into a mammalian host cell lacking a functional secreted human alkaline phosphatase gene;

f) screening transfected mammalian cells from step (e) for alkaline phosphatase activity and selecting the cells exhibiting the activity;

g) analyzing the DNA recovered from the transfected cells of step (f) which have alkaline phophatase activity to determine whether a functional mammalian signal sequence is present and;

h) screening a mammalian cDNA library to identify a full-length cDNA comprising the functional mammalian signal sequence of step (g).

The invention also relates to a CDNA molecule encoding a novel secreted mammalian protein and a novel secreted mammalian protein identified by employing steps (a) through (h) as set forth above.

DETAILED DESCRIPTION OF THE INVENTION

Recombinant DNA techniques used herein are generally set forth in Sambrook et al., *Molecular Cloning: A Laboratory Manual,* Cold Spring Harbor Laboratory Press, Cold Spring Harbor, N.Y., (1989); by Ausubel et al., eds *Current Protocols in Molecular Biology,* Current Protocols Press, (1994); and by Berger and Kimmel, *Methods in Enzymology: Guide to Molecular Cloning Techniques,* Vol. 152, Academic Press, Inc., San Diego, Calif., (1987), the disclosures of which are hereby incorporated by reference.

Chemical synthesis of nucleic acid sequences can be accomplished using methods well known in the art, such as those set forth by Engels et al. *Angew. Chem. Intl.* Ed. 28:716–734 (1989) and Wells et al. *Gene* 34:315 (1985), the disclosures of which are hereby incorporated by reference. These methods include the phosphotriester, phosphoramidite and H-phosphonate methods of nucleic acid sequence synthesis. Large nucleic acid sequences, for example those larger than about 100 nucleotides in length, can be synthesized as several fragments and ligated together. A preferred method is polymer-supported synthesis using standard phosphoramidite chemistry.

As used herein, the terms "signal sequence", "leader sequence", and "secretion sequence" are used interchangably and refer to N-terminal amino acid sequences capable of directing a polypeptide into the secretory pathway characteristic of eucaryotic cells. The term "reporter polypeptide" refers to polypeptides normally secreted by eucaryotic host cells which confer a property or activity when secreted that may be readily assay (e.g, growth on selected media, enzymatic activity, reactivity with detecting reagents). Preferred examples of such reporter polypeptides are described below.

Methods for identifying signal sequence DNA and novel secreted proteins (termed "signal sequence trapping") are provided by the invention. The methods employ signal trap vectors comprising DNA encoding nonsecreted reporter polypeptides. cDNA fragments are inserted into a signal trap vector to generate a signal trap library and transformed into mammalian host cells. Expression of a secreted reporter polypeptide is indicative of the presence of a signal sequence. After identification of signal sequences, full-length DNA clones encoding the secreted polypeptides may be isolated and expressed.

Secretion of a reporter polypeptide may be determined by growth on selective medium requiring the presence of the secreted reporter polypeptide. The reporter polypeptide may be a secreted mammalian growth factor which stimulates cell proliferation by an autocrine mechanism. One class of reporter polypeptides is secreted fibroblast growth factors, such as FGF-3 (or int-2), FGF-4 (also referred to as hst-1 or Kaposi FGF), FGF-5, FGF-6 (or hst-2), FGF-7 (also referred to as keratinocyte growth factor), and FGF-8. In one embodiment, the reporter polypeptide is Kaposi FGF (kFGF) and the preferred host cell is an NIH 3T3 cell.

Secretion of a reporter polypeptide may also be detected by enzymatic activity. In one embodiment, the reporter polypeptide is secreted human alklaine phosphatase which hydrolyzes a chromogenic or fluorogenic substrate upon secretion.

The invention also relates to a cDNA molecule encoding a novel secreted mammalian protein and a novel secreted mammalian protein identified by the methods of the invention.

cDNA libraries of the invention may be derived from any mammalian tissue or cell line and are preferably human cDNA libraries. Messenger RNA (mRNA) isolation from a selected tissue or cell line is and CDNA synthesis are carried using published procedures. The population of cDNA molecules so obtained may be used without further modification in construction a signal trap library or, alternatively, cDNA molecules may be selected for the presence of 5' ends (PCT Publication No. WO96/40904) or may be selected for fragments with a desired size range prior to insertion into signal trap vectors. For example, DNA fragments of up to about 600 base pairs may be selected for insertion into kFGF signal trap vectors. The fragments may be isolated by ion exchange chromatography, size exclusion chromatography or gel electrophoresis. Optionally, cDNA may be fragmented to smaller sizes prior to fractionation.

Signal trap vectors of the invention will be suitable for replication and expression of secreted polypeptides in mammalian cells. DNA sequences characteristic of such vectors include: an origin of replication, one or more selection or marker genes, a promoter sequence, one or more enhancer elements, a transcription termination sequence, reporter genes indicative of secret on, and the like. The vectors may also be used in bacterial host cells and may harbor at least an origin of replication and one or more selection or marker genes that are functional in bacterial host cells such as E. coli. These components may be obtained from natural sources or be synthesized by known procedures.

Origin of Replication

Signal trap vectors of the invention will have an origin of replication functional in mammalian cells and may also have an origin of replication functional in bacterial host cells. various mammalian origins include those derived from viruses, including SV40, polyoma, adenovirus, vesicular stomatitis virus (VSV) and bovine papilloma virus (BPV). Replication origins functional in bacteria are well known (e.g., ColE1, F, R1) and may give low or high plasmid copy numbers. A preferred origin of replication functional in bacteria is a ColE1-type such as that present on plasmid pBR322.

Selection Gene

A selection or marker gene encodes a polypeptide which allows for maintenance of the plasmid in a population of cells. Other selection genes may be used to amplify the genes to be expressed. Examples of suitable selectable markers for amplification in mammalian cells include dihydrofolate reductase (DHFR) and thymidine kinase.

For example, cells transformed with the DHFR selection gene are first identified by culturing all of the transformants in a culture medium that contains methotrexate, a competitive antagonist of DHFR. An appropriate host cell when wild-type DHFR is used is the Chinese hamster ovary cell line deficient in DHFR activity (Urlaub and Chasin (1980), *Proc. Natl. Acad. Sci., USA,* 77:4216–4220, the disclosure of which is hereby incorporated by reference). The transformed cells are then exposed to increased levels of methotrexate. This leads to the synthesis of multiple copies of the DHFR gene and, concomitantly, multiple copies of other DNA present in the expression vector.

Promoter

Suitable promoters for use with mammalian host cells are well known and include those obtained from the genomes of viruses such as polyoma virus, fowlpox virus, adenovirus (such as Adenovirus 2), BPV, avian sarcoma virus, cytomegalovirus, a retrovirus, hepatitis B virus and, most preferably, SV40. Other suitable mammalian promoters include inducible promoters wherein expression is regulated by an external stimulus. Examples of such promoters include heat-shock, metallothionien, and steroid hormone promoters. Other mammalian promoters may also be included in signal trap vectors. Promoters in signal trap vectors will include additional DNA sequence which provide for optimal activity, such as cis-acting enhancer elements and sequences necessary for promoter activation or induction (see below). Promoters suitable for use with prokaryotic hosts include the beta-lactamase and lactose promoter systems; alkaline phosphatase, a tryptophan (trp) promoter system; a bacterial luminescence (luxR) gene system and hybrid promoters such as the tac promoter. Other known bacterial promoters are also suitable.

Sequences of promoters mentioned herein have been published, thereby enabling one skilled in the art to ligate them to the desired DNA sequence(s) using linkers or adapters as needed to supply any required restriction sites.

Enhancer Element

Enhancers are cis-acting elements of DNA, usually from about 10–300 bp in length, that act on the promoter to increase its transcription. Several enhancer sequences available from mammalian genes are known (e.g., globin, elastase, albumina, a-feto-protein and insulin). Addittonally, viral enhancers such as the SV40 enhancer, the cytomegalovirus early promoter enhancer, the polyoma enhancer and adenovirus enhancers are exemplary enhancing elements for the activation of eukaryotic promoters. Enhancers may be positioned either 5' or 3' to the transcription unit.

Reporter Genes

The reporter genes in signal trap vectors of the invention encode nonsecreted reporter polypeptides by virtue of lacking a functional signal sequence. In a preferred embodiment, DNA encoding a nonsecreted reporter polypeptide is lacking the signal sequence including the initiator methionine. The reporter polypeptide may also lack one or more additional amino acids from the mature amino terminus of the protein, provided that deletion of these amino acids does not alter the activity of the reporter polypeptide. Techniques for deleting DNA encoding signal peptides are available to one skilled in the art. Secretion of the reporter polypeptide will occur upon in-frame insertion of a functional mammalian signal sequence and expression of the resulting fusion polypeptide. The reporter polypeptides described herein are normally produced in mammalian cells, although polypeptides from bacteria or yeast may also be used.

Reporter polypeptides may be used to detect signal sequences by growth selection. One such example of a reporter gene is Kaposi-fibroblast growth factor (kFGF, also referred to as FGF-4). kFGF is a member of the FGF family and is normally secreted from cells in which it is synthesized (Delli-Bovi et al. *Cell* 50, 729–737 (1987)). kFGF is normally expressed only in fetal tissue, and its expression in adult tissue is often related to the development of cancer. When kFGF is expressed in NIH 3T3 cells, it causes proliferation and cell transformation through autocrine activation of the FGF receptors on the cell surface. Previous studies showed that the biological function of kFGF may depend on its ability to be secreted (Delli-Bovi et al. *Mol. Cell. Biol.* 8, 2933–2941 (1988); Talarico et al. *Mol. Cell. Biol.* 11, 1138–1145 (1991))

Since the expression and secretion of kFGF enables NIH 3T3 cells to grow in serum-free medium, it can be used as a reporter polypeptide indicative of secretion. A signal sequence deleted kFGF gene can be used to analyze or select cDNA fragments containing a secretion signal sequence. In such a system, cDNA fragments are inserted into a vector containing a signal sequence deleted kFGF gene and transfected into NIH 3T3 cells. The cells are incubated with serum free medium. Since only cells which express secreted kFGF can grow, the cDNA fragments inserted must contain a signal sequence which enable the mutant to be secreted. The cDNA can then be recovered and analyzed for the presence of a signal sequence.

Although kFGF is used as an example, it is contemplated that other mammalian growth factors which stimulate cell proliferation by an autocrine mechanism may also be used as reporter polypeptides. For example, other secreted FGFs may also be reporter polypeptides.

A rat kFGF gene was constructed such that the signal sequence was deleted. Native rat kFGF supported NIH 3T3 cell growth in serum free medium while the rat kFGF gene lacking a signal sequence did not support growth. DNA fragments encoding the amino-terminal 24, 37, 98, or 134 amino acids of the epidermal growth factor receptor (EGFR) were prepared by polymerase chain reaction (PCR) and inserted into the kFGF clone lacking the signal sequence. The resulting genes were transfected into NIH 3T3 cells. The chimeric proteins containing EGFR signal sequences fused to mutant kFGF supported NIH 3T3 cell growth in serum free medium. These results demonstrated that the mutant kFGF and NIH 3T3 cells can be used to isolate cDNAs which containing the secreting signal sequences.

Another example of a reporter polypeptide is a phosphatase, such as human placental alkaline phosphatase.
Transcription Termination Expression vectors used in mammalian host cells each will typically contain a sequence necessary for the termination of transcription and for stabilizing the mRNA. Transcription termination sites may be homologous or heterologous to the reporter polypeptide being used, and may be located immediately 3' to the translational stop codon of the reporter polypeptide or located further downstream from the translational stop. Examples of transcription terminators include DNA sequences derived from histone and β-globin termination regions.

Polyadenylation of the 3' end of eucaryotic mRNAs may be accomplished by a sequences from a variety of sources, including SV40 early transcription unit, hepatitis B surface antigen transcription unit and mouse β-globin
Signal Sequence As indicated above, the signal sequence is provided as part of cDNA library. cDNA fragments derived from a library are cloned into the signal trap vector to the 5' side of DNA encoding the mature, nonsecreted reporter polypeptide. Secretion is indicated by in-frame translation of a signal sequence and a reporter polypeptide.

The construction of signal trap vectors containing one or more of the above-listed components, with one of the reporter genes listed above, is accomplished by standard ligation techniques. Isolated plasmids or DNA fragments are cleaved, tailored and religated in the desired order to generate the vector required. To confirm that the correct sequence has been constructed, the ligation mixture may be used to transform E. coli, and successful transformants may be selected by known techniques as described above. Quantities of the vector from the transformants are then prepared, analyzed by restriction endonuclease digestion and/or sequenced to confirm the presence of the desired construct. Signal trap vectors are constructed such that DNA sequences which control expression of selection or marker genes, cDNA inserts and reporter genes are operably linked to said cDNA and genes. In addition, the CDNA libraries are generated in signal trap vectors such that potential signal sequences are inserted in frame to reporter polypeptide coding sequences.

Examples of signal trap vectors include pEV7 and pEV15 which have been deposited with the American Type Culture Collection, Manassas, Va. 20110-2209 on Feb. 13, 1998 under accession nos. 98659 and 98660 respectively. Deposit of this material does not create any presumption that the material is necessary to satisfy 35 U.S.C. 112 or that deposit in accordance with these regulation is or was required.

In one embodiment, pEV7 or pEV15 vectors contain deletion mutants of kFGF cDNA as the reporter gene. One vector, ΔkFGF4, contains a fragment encoding kFGF amino acids 24–202 while a second vector, ΔkFGF7L, contains DNA encoding kFGF amino acids 71–202 (See Example 1). In both vectors, the expression of the reporter gene is controlled by a retrovirus LTR promoter. Two unique restriction sites, Sal I and Not I, were engineered between the promoter and the reporter gene. It will be recognized that other vectors may be constructed having alternate replication origins, selection genes and promoters, for example, which would be equally useful in signal trapping.

Host cells of the invention may be any suitable mammalian cell. Vertebrate cells may be used, as the propagation of vertebrate cells in culture (tissue culture) is a well-known procedure. Examples of useful mammalian host cell lines include but are not limited to monkey kidney CV1 line transformed by SV40 (COS-7), human embryonic kidney line (293 cells or 293 cells subcloned for growth in suspension culture), baby hamster kidney cells and Chinese hamster ovary cells. Other suitable mammalian cell lines include but are not limited to HeLa, mouse L-929 cells, 3T3 lines derived from Swiss, Balb-c or NIH mice, and BHK or HaK hamster cell lines. In one embodiment, the host cell is an NIH 3T3 cell.

Host cells for amplifying cDNA libraries are typically bacterial host cells, and preferably E. coli. Said host cells include but are not limited to eubacteria such as Gram-negative or Gram-positive organisms, e.g., E. coli (HB101, DH5α, DH10B and MC1061); Bacilli such as B. subtilis; Pseudomonas species, such as P. aeruginosa; Streptcmyces spp.; Salmonella typhimurium; or Serratia marcescans. As a specific embodiment, a desired protein may be expressed in E. coli.

Techniques for transforming or transfecting host cells with plasmid DNA are known in the art. A mammalian host cell may be transfected with a desired nucleic acid under appropriate conditions permitting expression of the nucleic acid. The selection of suitable host cells and methods for transformation, culture, amplification, screening and product production and purification are well known in the art (Gething and Sambrook Nature, 293:620–625 (1981) or, alternatively, Kaufman el al. Mol. Cell. Biol., 5:1750–1759 (1985), or U.S. Pat. No. 4,419,446, the disclosures of which are hereby incorporated by reference). For example, for mammalian cells without cell walls, the calcium phosphate precipitation method may be used. Electroporation, micro injection and other known techniques may also be used.

Transformed or transfected host cells are cultured in nutrient medium in a manner that allows stable maintenance of the resident recombinant plasmid, amplification of plasmid copy number, and expression and secretion of recombinant polypeptides encoded by said plasmids. In general, mammalian host cells are cultured in DMEM or F-12 medium optionally supplemented with serum. In general, bacterial host cells are cultured on rich (LB) medium or defined medium optionally supplemented with antibiotics for plasmid selection.

Detection of signal sequence DNA may be accomplished by a variety of methods depending upon reporter polypeptide and the host cell used. Although the reporter protein could either be of yeast, mammalian, or bacterial origin, it is preferably of mammalian origin. The assays described below are carried out in mammalian host cells that either naturally lack the reporter gene or the reporter gene is inactivated by mutation (e.g., deletion, insertion, or one or more base changes which alter the amino acid sequence).

Growth selection The secreted reporter polypeptides in this category are essential for growth of the host cells on a defined medium. In the present invention, secretion of kFGF is required for growth of NIH 3T3 cells in serum-free medium.

Enzyme activity. An enzymatic reporter polypeptide, upon successful secretion, hydrolyzes a substrate to effect a change in the color of a colony or its immediately adjacent area. Analogous to the growth-based assays, the secretion signal of the reporter is removed and replaced with the cDNA library. The recombinants containing reporter gene fused to the mammalian secretory signals that allow successful secretion are detected by adding appropriate substrate for the reporter enzyme into the growth media which upon cleavage gives a discernible phenotype. In this scheme, no selection pressure is applied for secretion (as in the growth assay) and all recombinants grow, whether or not they secrete the reporter enzyme. Positive colonies are distinguished visually. One example of a reporter polyeptide of this type is secreted alkaline phosphatase. Bacterial alkaline phosphatase or human placental alkaline phosphastase may be used.

Phosphatases are also amenable to FACS sorting based selection using a fluorescent phosphatase substrate to label the positive cells. Thus recombinants that allow secretion of phosphatase can be doubly selected by sorting followed by a color assay on plates.

Putative signal sequences obtained by one of the above screening methods are further characterized by isolation and sequencing of the cloned cDNA inserts using conventional techniques and analysis of the sequences so obtained. Typically, the sequence of the cDNA insert directing secretion of the reporter polypeptide will be compared to known signal sequences present in publicly available databases such as SwissProt or GenBank (translated). Sequence alignment programs such as those available in GCG Sequence Analysis programs (University of Wisconsin, Madison, Wis.) are useful for identifying regions of homology between the cDNA inserts that scored positive on secretion screens and known signal sequences.

As further confirmation that a novel sequence is indeed a signal sequence, part or all of the sequence of the cDNA insert directing secretion of the reporter polypeptide may be used as probe to identify the DNA sequence encoding the full-length polypeptide. The probe may be used in hybridization or PCR reactions to identify the coding sequence present in a cDNA, genomic DNA, or synthetic DNA library Expression of the DNA sequence encoding the full-length polypeptide in a mammalian host cell and secretion of the resulting polypeptide will confirm that the novel sequence identified in the secretion screen is a signal sequence.

Conditions for screening DNA libraries by hybridization using as probes cDNA fragments having a size of up to about 600 base pairs are set forth in Sambrook et al. supra, pp.387–389. Hybridization and washing are typically carried out under conditions that favor annealing of highly homologous regions of DNA taking into account factors such as the size of the cDNA fragments used as probes and the complexity of the library being screened. Preferably, the washing is carried out under high stringency conditions. Examples of stringent washing solutions, which are usually low in ionic strength and are used at relatively high temperatures, are as follows: one such stringent wash is 0.015 M NaCl, 0.005 M Na citrate and 0.1% SDS at 55–65° C.; another such stringent wash is 1 mM $Na_2EDTA$, 40 mM $NaHPO_4$, pH 7.2, and 1% SDS at about 40–50° C.; and one other stringent wash is 0.2×SSC and 0.1% SDS at about 50–65° C.

Hybridization array also be carried out using oligonucleotide probes derived from the aforementioned cDNA fragments. There are also exemplary protocols for stringent washing conditions where oligonucleotide probes are used for hybridization. For example, a first protocol uses 6×SSC with 0.05 percent sodium pyrophosphate at a temperature of between about 35° C. and 63° C., depending on the length of the probe. For example, 14 base probes are washed at 35–40° C., 17 base probes at 45–50° C., 20 base probes at 52–57° C., and 23 base probes at 57–63° C. The temperature can be increased 2–3° C. where the background non-specific binding appears high. A second protocol uses tetramethylammonlum chloride (TMAC) for washing. One such stringent washing solution is 3 M TMAC., 50 mM Tris-HCl, pH 8.0 and 0.2% SDS.

A cDNA library may also be screened genes encoding full-length secreted polypeptides by PCR using primers based upon the sequences obtained by signal trapping. Procedures for amplifying sequences by PCR are described in Aushel et al. supra.

Novel full-length secreted mammalian polypeptides are assayed for biological activity by various methods. In one method, the polypeptides are expressed by recombinant methods known in the art, such as transient expression in transfected COS cells or, if greater quantities of protein are desired, expression in stable transfectants such as CHO cells. Conditioned growth medium may be assayed directly for biological activity or the polypeptide may be partially or substantially purified using procedures known in the art prior to assay for activity. In this approach, a particular assay may be employed based upon a postulated activity for the secreted polypeptide. Biological activity may be surmised biased upon sequence homology to other proteins of known function, patterns of expression in tissues of developing and mature animals (especially when expression is limited to one or a few tissues), a combination of sequence homology and tissue expression, or some other criteria. In vitro assays are typically used to initially identify an activity of a novel protein and may be followed up by appropriate in vivo assays.

Alternatively, novel secreted proteins may be introduced into transgenic animals in order to directly determine in vivo activity in a whole animal. In one embodiment, a novel secreted mouse or rat protein is expressed as a transgene in a mouse or a rat. Suitable transgenic expression vecuors, transfection procedures and expression of foreign transgenes have been described in PCT Publication No. 97/23614, the relevant portions of which are hereby incorporated by reference. The physiological effects of systemic expression of a novel secreted protein are evaluated by pathology analysis of transgenic expressors, including histologic, histochemical and immunohistochemical analysis.

The following examples are offered to more fully illustrate the invention, but are not to be construed as limiting the scope thereof.

EXAMPLE 1

Signal Sequence Trapping using kFGF as a Reporter Polypeptide

Construction of ΔkFGF signal trap vectors

Rat kFGF cDNA was isolated from fetal rat kidney cDNA library and its sequence determined (see SEQ ID NO:1). The full length cDNA was cloned into a expression vector pEV7. Deletion mutants of kFGF lacking the signal sequence (designated herein as AkFGF) were made by PCR amplification. Three oligonucleotides were synthesized and used as the primers. The oligonucleotide 1484-68

AGGCAAAGCTTCCGAGAGTCACAGTCTAGG SEQ ID NO:3) was designed to be complementary to the sequence around the carboxy-terminus of the coding region which contains a HindIII site. It was used as the 3' primer. The oligonucleotide 1484-72:

ATTATGTCGACATGGCGGCCGCGGAC-CGAGGGACCGCCGC (SEQ ID NO:4) and oligonucleotide 1558-01:

ATTATGTCGACATGGCGGCCGCGGAC-TACCTGCTGGGCCTCAAAA (SEQ ID NO:5) were designed to delete 23 and 70 amino acids, respectively, from the amino terminus of full-length kFGF. Restriction enzyme sites Sal I and Not I were engineered at 5' end of these oligonucleotides. They were used as 5' primers.

PCR amplification was performed on a GeneAmp 9600 system (Perkin Elmer, Foster City, Calif.). The 100 μl reaction mixture contains 0.1 μg of pEV7/kFGF plasmid DNA, 0.5 μM of each primer, 1×Pfu buffer, 0.2 mM of each dNTP, 10% dimethyl sulfoxide and 2.5 units of Pfu DNA polymerase (Perkin Elmer). The reaction mixtures were heated at 95° C. for 1 minute, amplified four times with cycle parameters of 95° C. for 45 seconds, 60° C. for 45 seconds, and 72° C. for 2 minutes, followed by 24 cycles at 95° C. for 45 seconds, 68° C. for 45 second, and 72° C. for 2 minutes, and finally incubation at 72° C. for 3.0 minutes. The amplified DNA was phenol/chloroform extracted, ethanol precipitated, and digested with Sal I and Not I. The small linkers were removed by a S-400 MicroSpin column (Pharmacia).

The kFGF fragments were ligated into expression vector pEV15 which had been digested with Sal I and Not I enzymes and the ligation mixture was introduced into *E. coli* Dh10 cells (Bethesda Research Laboratories) by electroporation. Plasmid DNA was prepared and clones containing the correct insert were confirmed by restriction enzyme digestion and agarose gel electrophoresis. The two signal trap vectors were designated ΔkFGF4 and ΔkFCGF7 which encode rat kFGF amino acids 24–202 and 71–202 respectively (SEQ ID NO:2).

Secretion of kFGF Polypeptides With Heterologous Signal Sequences

DNA fragments encoding amino terminal portions of epidermal growth factor receptor (EGFR), erythropoietin (EPO), and granulocyte colony stimulating factor (G-CSF) including the signal peptides were prepared by PCR synthesis as described above. In each of these fragments, a Sal I side was inserted in front of the start codor. A Not I site was introduced at the 3' end of the fragments such that translation of the signal peptide fragment is in frame with that of the reporter gene. The NotI site introduces two extraneous alanine residues at the junction of the signal sequence and kVGF fragments. The fragments were then ligated with vectors, ΔkFGF4 and ΔkFGF7 which were also digested with Sal I and Not I. The ligated DNA were transformed into DH10B cells by electroporation. Plasmids DNA were prepared and analyzed by restriction enzyme digestion and agarose gel electrophoresis as described (Sambrook et al. supra).

The function of these signal peptides fused to the kFGF reporter polypeptide was determined by testing the ability of the expressed chimeric kFGF gene to support the growth of NIH 3T3 cells in serum-free medium. Plasmid DNA was transfected into NIH 3T3 cells using the calcium phosphate method as described (Sambrook et al. supra). Briefly, 200, 000 cells were plated in a 35 mm plates 24 hour before transfection with normal medium (DME14, 10% FCS, and 1×glutamine Pen-Strep). Cells were changed to fresh medium before the transfection. 100 ng Df the plasmid DNA was mixed with 4 μg of NIH 3T3 genomic DNA as the carrier. The cells were incubated for 6 hours at 37° C. and 5% $CO_2$ with the calcium-DNA complex. The medium was then replaced with fresh normal medium. The cells were then incubated for 15 hours, harvested with trypsin, and cells from one 35 mm plate were plated into five 100 mm plates. The cells were crown in normal medium for one day and in low serum medium (50% DMEM, 50% F-12 HAM, 0.5% fetal calf serum (FCS), 5 μg/ml bovine transferrin, and 10 μg /ml insulin) for five days. The plates were examined for colonies of NIT 3T3 cells either by microscope or staining with 1% methylene blue in methanol.

No growth of normal untransfected NIH 3T3 cells and cells transfected with empty vectors on serum-free medium was observed and cells started to lyse after one week of selection. In contrast, the cells transfected with plasmids carrying full-length kFGF or test DNA fragments containing signal sequences continue to grow in selection medium, and each transfected cell grow into a colony of 30–100 cells. These data suggested that the signal peptides tested can restore the biological function of kFGF to support the growth of NIH 3T3 cells in serum-free medium. DNA fragments up to 600 base pairs may be inserted into the signal trap vectors with no decrease in the activity of the reporter polypeptide fusion. Similar results were obtained when two of the fragments were tested in vector ΔkFGF7L. These results demonstrated that the vectors constructed can detect signal sequences in the NIH 3T3 cell growth selection assay.

Construction of cDNA Libraries

Poly A+ RNA was prepared from mouse placenta using a commercially available RNA extraction kit and mRNA purification kit (Pharmacia Biotech). The cDNA library was made following the protocol of SuperScript™ Plasmid System for cDNA Synthesis and Plasmid Cloning (GIBCO/BRL, Cat. No. 18248-013) with some modification. To make cDNA with random 3' ends followed by a Not I site, the oligonucleotide 1360-38:

GGA AGG AAA AAA GCG GCC GCA ACA NNK NNN NNN (SEQ ID NO:6) was made and used as the primer for first strand DNA synthesis. Five μg of poly A RNA and 500 μg of the primer was used in the first strand reaction. After second strand synthesis using published procedures, Sal I adapter ligation, and Not I digestion, cDNA was purified using a mini Q column and tPLC (Pharmacia). The cDNA was adjusted to buffer A, 0.6M NaCl, 20 mM Tris pH 8.0, and loaded of the column. The column was washed with 3 ml of buffer A at 0.1 ml/minute. The bound cDNA was eluted with 0.6 ml of buffer B, 20 mM Tris pH8.0, 7.5 M NaCl. The solution was divided into two 1.5 ml tubes. To each tube was added 2.5 μg yeast tRNA, 150 μl of 7.5 M $NH_4AC$, and 900 μl ethanol. The cDNA was precipitated, pelleted by centrifugation at 14000 rpm for 20 minutes, and washed with 0.5 ml of 70% ethanol.

The cDNA library prepared in this manner was ligated into the Sal I and Not I digested vector ΔkFGF4. The ligation was carried in 20 μl. containing 75 μg of vector DNA, 20 μg of cDNA, 1×ligase buffer, and 1 μl of T4 ligase at 16° C. for 20 hours. The ligated DNA was precipitated and introduced into *E. coli* by electroporation as described in the protocol. The transformed bacteria cells were grown in 5 ml SOC at 37° C. for 1 hour, and then frozen at −80° C. with 10% glycerol.

Screening cDNA Libraries Using kFGF Signal Trap

Plasmid DNA from the cDNA library was prepared in pools of 50,000 colony forming units (cfu) each. E.coli transformed with a cDNA library in the ΔkFGF4 signal trap vector were plated on 150 mm LB agar plates with 100 μg/ml ampicillin and incubated at 37° C. overnight. About 50,000 colony forming units (cfu) from agar plates were pooled into 50 ml LB in a 250 ml flask. The bacteria were grown for 3 hours with agitation, and pelleted by centrifugation at 4000 rpm for 10 minutes in 50 ml conical tubes Ten pools were prepared. Plasmid DNA was isolated from the pools using QIAGEN maxi prep.

Plasmid DNA was introduced into NIH 3T3 cells by calcium phosphate transfection as described above, in which 100 ng of each cDNA library pool was used to transfect about 200,000 cells in one 35 mm plate. After 24 hours, the cells from one 35 mm plate were split into five 100 mm plates and grown in normal medium for one day followed by low serum medium for 13 days. About 2000 colonies grew from transfected cells after the two week incubation.

Construction of Signal Peptide Enriched cDNA Library

To each 100 mm plate was added 2 ml of trypsin-EDTA followed by incubation are 37° C. for 5 minutes. The cells in the colonies were released from the surface of the plate by gentle swirling. Cells were transferred to 50 ml conical tubes with 2 ml of FCS to stop the trypsin activity. Tubes were centrifuged at 1000 rpm for 5 minutes to pellet the cells. The supernatant was discarded.

Cells equal or less then 1 gram were lysed with 20 ml of TRIzol reagent (BRL), homogenized for 30 seconds, and extracted with 4 ml of chloroform. The tubes were centrifuged at 4000 rpm for 30 minutes and the aqueous phase was transferred to a new tube. RNA was precipitated by adding 10 ml isopropanol, mixing, and centrifuging for 30 minutes at 4200 rpm. The RNA pellet was washed with 10 ml of 70% ethanol, dried briefly, and resuspended In 9.5 ml TE buffer. PolyA RNA was prepared by using a commercially available mRNA purification kit (Pharmacia). After elution of polyA RNA from the column in 750 μl of TE buffer, the sample was then ethanol precipitated in two 1.5 ml tubes by adding 40 pi sample buffer and 1 ml ethanol at −70 ° C. overnight.

The cDNA inserts of the positive clones were rescued by RT-PCR. A SuperScript™ preamplification system (BRL) was used to synthesize first strand cDNA. For each reaction, 1 μg polyA RNA, 1 μl (2 μM) primer 1605-21 (5' AATC-CGATGCCCACGTTGCAGTA 3';SEQ ID NO:7), and water were combined in a total, clurne of 15 μl. The mixture was incubated at 70° C. for 10 minutes and transferred to 50° C. The premixture containing 2.5 μl 10×buffer, 2.5 μl of 25 mM MgC12, 1.3 μl 10 mM dNTPs, and 2.5 ul 0.1 M dithiotheritol was added. The reaction was started by addition of 1.2 μl reverse transcriptase and incubated at 50° C. for 1 hour. The reaction was stopped by incubation at 70° C. for 15 minutes. The RNA was digested with 1 ul RNase H at 37° C. for 20 minutes.

The PCR was performed with Pfu polymerase (Perkin Elmer), in a total volume of 100 μl, 2 ul first strand reaction, 1×Pfu buffer, 0.5 uM each of primers 1239-08 (5' AAAATCTTAGACCGACGACTGTGTTT 3'; SEQ ID NO:8) and 1605-22 (5' GAGTCTCCGCAGC-CTTTTGAGG; SEQ ID NO:9), 0.2 mM dNTPs, 5% DMS, and 2.5 u Pfu polymerase were added. The sample was heated at 95° C. for 1 minute, and amplified for 30 cycles. Each cycle includes: 95° C. for 30 seconds, 66° C. for 45 seconds, 72° C. for 2 minutes. The reaction was incubated at 72° C. for 10 minutes at the end.

PCR DNA fragments were extracted once with phenol/chloroform (50/50) and ethanol precipitated. The DNA was then digested with NotI and SalI and small fragments and PCR primers were removed by using mini-Q column on FPLC as described above. A signal trap library was constructed by ligating the DNA fragments into Sal I and Not I digested vector, ΔkFGF7L. Each ligation included 10 ngr PCR fragments 50 ng vector, 1× ligase buffer, and 0.5 u T4 DNA ligase in a total volume of 10 μl. The ligation was carried at 16° C. overnight. The ligated DNA was was precipitated by adding 5 μl tRNA, 10 μl water, 12.5 μl 7.5 M NH$_4$AC, 70 μl ethanol (−20° C.), and centrifuged for 20 minutes. The pellet was washed with 0.5 ml 70% ethanol (−20° C.), and resuspend in 5 μl water. 1 μl was used to transform 20 ul of E. coli DH10B cells by electroporation. More than 1 million cfu were obtained.

319 clones were sequenced from the signal trap generated cDNA library and computer analyzed to determine the presence of signal sequences and transmembrane domains. 54 clones contained signal sequences corresponding to known secreted proteins. 29 clones contained novel signal sequences as predicted by computer analysis. Clones having either signal sequences or transmembrane domains together comprised about 25% of the clones sequenced. It is estimated that about 1–5% of the total clones in the normal cDNA library contain signal sequence. Therefore, by using this kFGF signal trap system, it is possible to enrich the clones with signal peptide by 5–25 fold. In addition, 81 clones were observed to have sequences encoding transmembrane domains of known genes or were predicted to encode transmembrane domains. Since both signal peptide and transmembrane domain contain hydrophobic amino acid residues, some transmembrane sequences may function as a signal peptide. The signal trap cloning system described here maw also enrich for clones containing a transmembrane domain.

EXAMPLE 2

Signal Sequence Trapping using Human Placental Alkaline Phosphatase as a Reporter Polypeptide Placental Alkaline Phosphatase (PLAP) Vector Construction cDNA was generated by reverse transcription of human placental RNA using oligo(dt) and subjected to PCR amplification using oligonucleotides:

5'-ACTGGCGGCCGCAGGCATCATCCCAGTTGAGG AG-31' (SEQ ID NO:10) and

5'-ACTGGTCACTCGAGGGTACCTTAGCTAGCCCC CGGG-3' (SEQ ID NO:11) whose sequences are in part identical to or antisense to nucleotide positions 102–122 and 1554–1571 of the human placental alkalins phosphatase cDNA (Millan, J. Biol. Chem. 261, 3112–3115 (1986) and GenBank Accession No. M13077). The PCR was (carried out cat 94° C. for 30 seconds, 60° C. for 30 seconds and 72° C. for 3 minutes for 35 cycles. The resulting PCR fragment (corresponding to the amino acid sequence from position 22 to 490, and lacking the signal peptide, was digested with NotI and KpnI and cloned into expression vector pcDNA3.1(−) (Invitrogen Coro., Carlsbad Calif., Cat. no. v795-20).

cDNA Library Constructor

Rat hypothalamus double stranded cDNA was synthesized according to a commercially available procedure (GIBCO/BRL). The double stranded cDNA was size-selected for fragments in the range of 0.2–0.8 kb by standard agarose gel eletrophoresls (Sambrook et al. supra). The Sal I and Not I digested double stranded cDNA fragments were then Ligated to pcDNA 3.1(−) at Xho I and Not I sites and transformed into the DH10B strain of E. coli by electroporation.

DNA Preparation

Individual bacterial clones were picked and arrayed into 384-well format. Clones were grown for 16 hours at 37° C. in LB, 7.5% glycerol. Bacterial clones were then inoculated into 50% LB/50% TB and grown for 22 hours at 37° C. for amplification. Amplified bacteria were lysed and neutralized using published procedures. Plasmid DNA was recovered and purified using carboxyl-coated magnetic beads (Bio-Mag DNA Sep beads, PerSeptive Biosystems, Cat no. 8MB4125).

Screening cDNA Library with PLAP Signal Trapping

COS7 cells were seeded into 96-well format ($4.5 \times 10^3$ cells/well) in complete mediums (DMEM, 10% FBS, 1× glutamine-penicillin-streptophan) and incubated at 37° C. for ~18 hours. Introduction of plasmid DNA into COS7 cells was accomplished using SuperFect transfection reagent (QIAGEN, Cat no. 301305). 500 ng of plasmid DNA (diluted to 30 ul final volume in plain DMEM) was mixed with 3 $\mu$l (3 mg/ml stack) of SuperFect (diluted to 20 $\mu$l final volume in plain DMEM) and incubated at room temperature for 10 minutes. The DNA/SuperFect complex was then diluted with 150 $\mu$l of complete medium and incubated on COS7 cells for 2 hours at 37° C. Cells were then washed with 200 ul of phenol red-free DMEM (GIBCO cat no. 31053-028), 1×glutamine-penicillin-streptophan. Cells were Conditioned in 100 $\mu$l of phenol-red-free DMEM, 1×glutamine-penicillin-streptophan for 24 hours at 37° C.

The levels of secreted alkaline phosphatase in transfected COS cells Where detected using the fluorogenic substrate 4-methylumbelliferyl phosphate (MUP), dicyclohexylammonium salt, trihydrate (Molecular Probes cat no. M-8425). 100 ul of 2×reaction buffer (2M diethanolamine (Sigma cat no. D0681), 1 mM, MgCl2, 20 mM L-homoarginine (Sigma cat no. H1007), 1 mg/ml bovine serum albumin (BSA; Sigma cat no. A-6003), 200 uM MUP) was added directly to the cells/conditioned media and incubated for 1 hour at 37° C. Fluorescence levels were detected using a Cytofluor II instrument (PerSeptive Biosystems) at an excitation wavelength of 360 and an emission wavelength of 460 nm. Transfectants having at least a two-fold increase in placental alkaline phosphatase activity over background were considered positive and submitted for DNA sequencing.

14,000 clones from two signal trap libraries were assayed for PLAP activity. DNA sequencing revealed that about 36% of the PLAP positive clones contained either signal sequences or transmembrane domains. Of these, 73% had signal sequences.

While the invention has been described in what is considered to be its preferred embodiments, it is not to be limited to the disclosed embodiments, but on The contrary, is Intended to cover various modifications and equivalents included within the spirit and scope of the appended claims, which scope is to be accorded the broadest interpretation so as to encompass all such modifications and equivalents.

What is claimed is:

1. A method for identifying a secreted mammalian protein comprising the steps of:
   a) constructing a mammalian cDNA library;
   b) inserting the cDNA library of step (a) into a signal trap vector to generate a signal trap library, wherein the vector comprises DNA encoding a reporter polypeptide, the reporter polypeptide being a secreted mammalian growth factor lacking a functional signal sequence;
   c) amplifying the signal trap library of step (b);
   d) transfecting the library of step (c) into a mammalian host cell lacking a functional reporter polypeptide of step (b);
   e) selecting transfected mammalian host cells from step (d) for growth in selective medium requiring secretion of the reporter polypeptide;
   f) analyzing the DNA recovered from the transfected cells of step (e) which exhibit growth on selective medium to determine whether a functional mammalian signal sequence is present and;
   g) screening a mammalian cDNA library to identify a full-length cDNA comprising the functional mammalian signal sequence of step (f), wherein the cDNA encodes a secreted mammalian protein.

2. The method of claim 1 wherein the reporter polypeptide is a secreted fibroblast growth factor selected from the group consisting of FGF-3, FGF-4, FGF-5, FGF-6, FGF-7 and FGF-8 lacking a functional signal sequence.

3. The method of claim 1 wherein the reporter polypeptide is Kaposi-FGF (FGF-4) lacking a functional signal sequence.

4. The method of claim 1 wherein the mammalian host cell is a NIH 3T3 cell.

5. The method of claim 1 wherein the selective medium is serum-free medium.

* * * * *

UNITED STATES PATENT AND TRADEMARK OFFICE
CERTIFICATE OF CORRECTION

PATENT NO. : 6,150,098  
DATED : November 21, 2000  
INVENTOR(S) : Ke Zhang

Page 1 of 2

It is certified that error appears in the above-identified patent and that said Letters Patent is hereby corrected as shown below:

Title page,
Item [75], remove [Robert Pacifici, both]

Column 5,
Line 15, change [secret on] to -- secretion --

Column 6,
Line 16, change [Addittonally] to -- Additionally --

Column 10,
Line 1, change [array] to -- may --
Line 20, change [Aushel] to -- Ausbel --
Line 45, change [vecuors] to -- vectors --

Column 11,
Line 1, change [AGGCAAAGCTTCCG...] to -- AGGCAAAGCTTCGG... --
Line 26, change [3.0] to -- 10 --
Line 38, change [ΔkFCGF7] to -- ΔkFGF7 --
Line 53, change [kVGF] to -- kFGF --
Line 67, change [DME14] to -- DMEM --

Column 12,
Line 2, change [Df] to -- of --
Line 9, change [crown] to -- grown --
Line 13, change [NIT] to -- NIH --
Line 42, change [NNK] to -- NNN --
Line 48, change [tPLC] to -- FPLC --
Line 50, change [of] to -- on --

Column 13,
Line 35, change [9.5] to -- 0.5 --
Line 41, change [pi] to -- µl --

Column 14,
Line 5, change [ngr] to -- ng --
Line 32, change [maw] to -- may --
Line 40, change [dt] to -- dT --
Line 43, change [31] to -- 3 --
Line 47, change [alkalins] to -- alkaline --
Line 51, change [cat] to -- at --

UNITED STATES PATENT AND TRADEMARK OFFICE
CERTIFICATE OF CORRECTION

PATENT NO. : 6,150,098
DATED : November 21, 2000
INVENTOR(S) : Ke Zhang

It is certified that error appears in the above-identified patent and that said Letters Patent is hereby corrected as shown below:

Line 58, change [Constructor] to -- Construction --
Line 63, change [eletrophoresls] to -- eletrophoresis --

Column 16,
Line 2, change [Where] to -- were --

Signed and Sealed this

Second Day of October, 2001

Attest:

Attesting Officer

NICHOLAS P. GODICI
Acting Director of the United States Patent and Trademark Office

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 1656 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 38..643

(xi) SEQUENCE DESCRIPTION: SEQ ID NO:1:

```
CCCGCCGCTC GGGCTCACGC ACGGCCCGCG GGCCGGA ATG GCG AAG CGC GGG CCG        55
                                        Met Ala Lys Arg Gly Pro
                                         1               5

ACT ACA GGG ACG CTG CTG CCC GGG GTC CTG CTG GCC CTG GTG GTG GCC         103
Thr Thr Gly Thr Leu Leu Pro Gly Val Leu Leu Ala Leu Val Val Ala
            10                  15                  20

CTG GCG GAC CGA GGG ACC GCC GCA CCC AAC GGC ACG CGG CAC GCC GAA         151
Leu Ala Asp Arg Gly Thr Ala Ala Pro Asn Gly Thr Arg His Ala Glu
        25                  30                  35

TTG GGG CAC GGC TGG GAC GGC CTG GTG GCC CGC TCG CTG GCA CGC TTG         199
Leu Gly His Gly Trp Asp Gly Leu Val Ala Arg Ser Leu Ala Arg Leu
    40                  45                  50

CCG GTG GCC GCG CAG CCC CCG CAG GCG GCG GTC CGC AGC GGC GCA GGG         247
Pro Val Ala Ala Gln Pro Pro Gln Ala Ala Val Arg Ser Gly Ala Gly
55                  60                  65                  70
```

```
GAC TAC CTG CTG GGC CTC AAA AGG CTG CGG AGA CTC TAC TGC AAC GTG           295
Asp Tyr Leu Leu Gly Leu Lys Arg Leu Arg Arg Leu Tyr Cys Asn Val
             75                  80                  85

GGC ATC GGA TTC CAC CTG CAG GTG CTG CCC GAC GGC CGC ATC GGC GGT           343
Gly Ile Gly Phe His Leu Gln Val Leu Pro Asp Gly Arg Ile Gly Gly
                 90                  95                 100

GTG CAC GCG GAC ACG AGG GAC AGC CTT CTG GAG CTC TCT CCG GTG CAG           391
Val His Ala Asp Thr Arg Asp Ser Leu Leu Glu Leu Ser Pro Val Gln
            105                 110                 115

CGG GGT GTG GTG AGC ATC TTC GGA GTG GCC AGC CGG TTC TTC GTG GCC           439
Arg Gly Val Val Ser Ile Phe Gly Val Ala Ser Arg Phe Phe Val Ala
        120                 125                 130

ATG AGC AGC AGG GGC AAG CTC TTC GGT GTG CCT TTC TTT ACC GAC GAG           487
Met Ser Ser Arg Gly Lys Leu Phe Gly Val Pro Phe Phe Thr Asp Glu
135                 140                 145                 150

TGT AAA TTC AAA GAA ATA CTT CTC CCC AAC AAC TAC AAT GCC TAC GAG           535
Cys Lys Phe Lys Glu Ile Leu Leu Pro Asn Asn Tyr Asn Ala Tyr Glu
                155                 160                 165

TCC TAC GCA TAC CCG GGC ATG TTC ATG GCC CTC AGT AAG AAC GGG CGG           583
Ser Tyr Ala Tyr Pro Gly Met Phe Met Ala Leu Ser Lys Asn Gly Arg
            170                 175                 180

ACC AAG AAG GGG AAC CGA GTT TCG CCG ACC ATG AAG GTA ACC CAC TTC           631
Thr Lys Lys Gly Asn Arg Val Ser Pro Thr Met Lys Val Thr His Phe
        185                 190                 195

CTT CCT AGA CTG TGACTCTCCG AAGCCCTGCC TCAGCCTCGG AAGCACACCC               683
Leu Pro Arg Leu
    200

GACCCCTCAG GAGGAGCACT TTCTCTCGAT GGATAATTGT TTGCAAAAAC AAGCCTAAGA         743

TATTTAAATT AATTATTTAA ATATGTATAT ATGGACAGCC AATTATTTAT AAGCCTATGT         803

ATTTTCATTT TCTGGCGGAA AATGACCAAA AGAACAAACA AATCAAATGC AGCTCGGACC         863

TCTTTGGTAC AGTGGGACAA ACTTTTTCCT TCACTCTCAA AGATCGGGCT GTGCTGCTGT         923

TTCATATGTG CCTCTAAAAC GTGGTGACAT CAGATTCCAA GGGTGCCTGG CCCCTCTGTC         983

TGGAAAGGCC TGCTTGGGTC CTCTGAGTCA GTGAGAGGAG GACCCTAAGC TTCCTCCTGT        1043

CCCGGAGCAT CCTGCAGCAG CCGCTCCCTC AGCTCCCTTT GGTATGAACC CTGTCGGATC        1103

GGTTTACTCC AGGGACAGAA GTGCGTCCTG GAAGTCCTCC CGCCTCTGTT TTTAGATCTC        1163

CAAGACTGAT CTTTGAACTC TCTTGCAGTC AATCTTCTTG GACCTACCGG ATGGGAGACC        1223

CTTAGACAAC TTTATAAACT CCTGTTTGCC TTCTTTTTTA CTGGCCAACA GGGCGCATGG        1283

CTTGTAGCCA CTGGAACTTT GTAAATTCCC TGGAAAAAGG AACTAGGAAT GGACAAGATG        1343

CGTGTGCCAC AACTCCAACT CTAGGGATGA AATTGTTTTG TGATAGAGGA TGACATGTCG        1403

GGGATATAAC AATGTATTTT GCAAAAATCA AATTGAGAAA AACAGGCTTC CCTGAATTTG        1463

GGGGTCTTTT GTGTTGGGAC TCCATAATTT AAAGTTACTA CAGGTGTCGA CCCAGAGATG        1523

GTATGTGCTA TGCACACTGG ATGCTCCATC CAAGAGAAGC ATTCAATCAT GTATAGAGAG        1583

CCCCCACGGA CTGGGAGTGA CTGAGAAAGA TATTAAAATG ACAAACGTAT CTGGAAAAAA        1643

AAAAAAAAAA AAA                                                          1656
```

(2) INFORMATION FOR SEQ ID NO:2:

(i) SEQUENCE CHARACTERISTICS:
        (A) LENGTH: 202 amino acids
        (B) TYPE: amino acid
        (D) TOPOLOGY: linear (ii) MOLECULE TYPE: protein (xi) SEQUENCE DESCRIPTION: SEQ ID NO:2:

| | | | | | | | | | | | | | | |
|---|---|---|---|---|---|---|---|---|---|---|---|---|---|---|
|Met|Ala|Lys|Arg|Gly|Pro|Thr|Gly|Thr|Leu|Leu|Pro|Gly|Val|Leu|
|1| | | |5| | | |10| | | | |15| |

Leu Ala Leu Val Val Ala Leu Ala Asp Arg Gly Thr Ala Ala Pro Asn
                20                    25                  30

Gly Thr Arg His Ala Glu Leu Gly His Gly Trp Asp Gly Leu Val Ala
         35                  40                   45

Arg Ser Leu Ala Arg Leu Pro Val Ala Ala Gln Pro Pro Gln Ala Ala
    50                 55                  60

Val Arg Ser Gly Ala Gly Asp Tyr Leu Leu Gly Leu Lys Arg Leu Arg
65               70                75                80

Arg Leu Tyr Cys Asn Val Gly Ile Gly Phe His Leu Gln Val Leu Pro
         85                  90               95

Asp Gly Arg Ile Gly Gly Val His Ala Asp Thr Arg Asp Ser Leu Leu
       100                 105               110

Glu Leu Ser Pro Val Gln Arg Gly Val Val Ser Ile Phe Gly Val Ala
       115                 120               125

Ser Arg Phe Phe Val Ala Met Ser Ser Arg Gly Lys Leu Phe Gly Val
   130                 135               140

Pro Phe Phe Thr Asp Glu Cys Lys Phe Lys Glu Ile Leu Leu Pro Asn
145               150                155              160

Asn Tyr Asn Ala Tyr Glu Ser Tyr Ala Tyr Pro Gly Met Phe Met Ala
       165                 170               175

Leu Ser Lys Asn Gly Arg Thr Lys Lys Gly Asn Arg Val Ser Pro Thr
       180                 185               190

Met Lys Val Thr His Phe Leu Pro Arg Leu
   195                 200

(2) INFORMATION FOR SEQ ID NO:3:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

AGGCAAAGCT TCGGAGAGTC ACAGTCTAGG                                     30

(2) INFORMATION FOR SEQ ID NO:4:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

ATTATGTCGA CATGGCGGCC GCGGACCGAG GGACCGCCGC                   40

(2) INFORMATION FOR SEQ ID NO:5:

(i) SEQUENCE CHARACTERISTICS:
        (A) LENGTH: 45 base pairs
        (B) TYPE: nucleic acid
        (C) STRANDEDNESS: single (D) TOPOLOGY: linear (ii) MOLECULE TYPE: cDNA (xi) SEQUENCE DESCRIPTION: SEQ ID NO:5:

ATTATGTCGA CATGGCGGCC GCGGACTACC TGCTGGGCCT CAAAA                45

(2) INFORMATION FOR SEQ ID NO:6:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

GGAAGGAAAA AAGCGGCCGC AACANNNNNN NNN                             33

(2) INFORMATION FOR SEQ ID NO:7:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

AATCCGATGC CCACGTTGCA GTA                                        23

(2) INFORMATION FOR SEQ ID NO:8:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

AAAATCTTAG ACCGACGACT GTGTTT                                     26

(2) INFORMATION FOR SEQ ID NO:9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

GAGTCTCCGC AGCCTTTTGA GG                                         22

(2) INFORMATION FOR SEQ ID NO:10:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA -continued (xi) SEQUENCE DESCRIPTION: SEQ ID NO:10:

ACTGGCGGCC GCAGGCATCA TCCCAGTTGA GGAG     34

(2) INFORMATION FOR SEQ ID NO:11:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:11:

ACTGGTCACT CGAGGGTACC TTAGCTAGCC CCCGGG     36